United States Patent
Maignan (12)

(10) Patent No.: US 6,177,089 B1
(45) Date of Patent: *Jan. 23, 2001

(54) USE OF AT LEAST ONE SULPHONIC ACID FOR STIMULATING RENEWAL AND/OR EPIDERMAL REPAIR AND FOR COMBATTING CUTANEOUS AGING AND CONDITIONS

(75) Inventor: Jean Maignan, Tremblay en France (FR)

(73) Assignee: L'Oréal, Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/709,538

(22) Filed: Sep. 6, 1996

(30) Foreign Application Priority Data

Sep. 7, 1995 (FR) .................................................. 95 10483

(51) Int. Cl.[7] .............................. A61K 7/48; A01N 37/12; A01N 37/10
(52) U.S. Cl. ......................... 424/401; 514/562; 514/568; 514/844; 514/845; 514/847
(58) Field of Search ................................... 514/562, 844, 514/845, 847, 568; 424/401

(56) References Cited

U.S. PATENT DOCUMENTS 3,920,835 * 11/1975 Van Scott et al. .................... 424/311
4,053,630 * 10/1977 Yu et al. ............................... 424/289
4,224,339   9/1980 Van Scott et al. .
4,283,386 *  8/1981 Van Scott et al. ...................... 424/70
5,262,407   11/1993 Leveque et al. ...................... 514/159

FOREIGN PATENT DOCUMENTS 0368758   5/1990 (EP) .

OTHER PUBLICATIONS

Chemical Abstracts AN 1987:403580, Takahashi et al, "A test to monitor age–associated changes in human skin." KK. SCCJ (1986), 20(3), 186–93, Jan. 1986.*

English language Derwent Abstract of EP–A–0368758. No US Equiv.

English language Derwent Abstract of JP–A–01146816. No US Equiv.

* cited by examiner

Primary Examiner—Jyothsna Venkat
Assistant Examiner—P. Ponnaluri
(74) Attorney, Agent, or Firm—Finnegan, Henderson, Farabow, Garrett & Dunner, L.L.P.

(57) ABSTRACT

The use of specific sulphonic acids or hydrates thereof in or for the preparation of a cosmetic or dermatological composition for achieving various effects on the skin, such as promoting desquamation of the skin, stimulating epidermal renewal, combatting intrinsic and extrinsic cutaneous aging. A process for the non-therapeutic treatment of the skin intended to achieve such effects, such as to promote the desquamation of the skin.

28 Claims, No Drawings

USE OF AT LEAST ONE SULPHONIC ACID FOR STIMULATING RENEWAL AND/OR EPIDERMAL REPAIR AND FOR COMBATTING CUTANEOUS AGING AND CONDITIONS

The present invention is directed to the use of specific sulphonic acids in or for the preparation of a cosmetic and/or dermatological composition for such purposes as promoting desquamation of the skin and/or for combatting intrinsic and extrinsic aging of the skin, as well as treating various skin conditions. The present invention is also directed to a process for the non-therapeutic treatment of the skin for purposes such as desquamating the skin and treating the skin for cutaneous aging and various skin conditions.

Cutaneous aging resulting from the effects on the skin of intrinsic or extrinsic factors is reflected, for example, by the appearance of wrinkles and fine lines, by the yellowing of the skin, which develops a wizened appearance, by the appearance of pigmentary blemishes, by disorganization of the elastin and collagen fibres, which results in a loss of elasticity, suppleness and firmness, and by the appearance of telangiectasias.

Some of these signs of aging are more particularly related to intrinsic or physiological aging, that is to say, to the "normal" effects of age, whereas others are more specific to extrinsic aging, that is to say, aging generally caused by the environment, more particularly photoaging due to exposure to the sun, to light or to any other radiation. The present invention is concerned with both intrinsic or physiological aging and with extrinsic aging of the skin.

The changes in the skin due to intrinsic aging are the consequence of a genetically programmed senescence involving endogenous factors. This intrinsic aging causes, in particular, a slowing down in the renewal of the cells of the skin, which is essentially reflected by the appearance of undesirable clinical changes, such as the reduction in the subcutaneous adipose tissue and the appearance of fine lines or wrinkles, and by histopathological changes, such as an increase in the number and thickness of the elastic fibres, the loss of vertical fibres in the membrane of the elastic tissue and the presence of large irregular fibroblasts in the cells of this elastic tissue.

In contrast, extrinsic aging results in undesirable clinical changes, such as thick wrinkles and the formation of a flabby and tanned skin, and in histopathological changes, such as excessive accumulation of elastic matter in the upper dermis and degeneration of the collagen fibres.

Various agents intended for combatting cutaneous aging are known in the prior art. In this regard, U.S. Pat. No. 4,603,146 describes the use of retinoic acid and its derivatives in cosmetic compositions for the purpose of controlling cutaneous aging.

Further, many patents and publications, for example, European Patent application EP-A-413,528, and many commercial cosmetic compositions teach the use of α-hydroxy acids, such as lactic acid, glycolic acid or citric acid, for treating cutaneous aging.

Finally, β-hydroxy acids, and more particularly salicylic acid and its derivatives, are known for their desquamating properties, see, for example, International patent application WO-A-93/10756 and U.S. Pat. No. 4,767,750.

All these compounds have an action against aging of the skin which includes a desquamation, that is to say the removal of the "dead" cells situated at the surface of the stratum corneum. This desquamating property is also known, often wrongly, as a keratolytic property. However, these compounds also exhibit side effects, which consist of stinging, tightness, overheating and redness, which the user often finds unpleasant.

It can thus be seen that there is still a need for anti-aging agents which act on the skin, at least as effectively as that of the compounds of the prior art, but which do not exhibit their disadvantages.

The Inventor has unexpectedly discovered that the topical application of cysteic or homocysteic acid or of one of their derivatives makes it possible to desquamate the skin as well as to stimulate epidermal cell renewal and epidermal repair.

Cysteic and homocysteic acids are certainly already known in the pharmaceutical field for the treatment of dry skin, warts, actinic or non-actinic keratoses, acne, ichthyoses and palmar and plantar hyperkeratoses, see, for example, U.S. Pat. No. 4,224,339. However, no one, until now, has envisaged or suggested the use of these acids for desquamation of the skin, stimulation of epidermal renewal, epidermal repair and/or the treatment of cutaneous aging.

A subject of the present invention is consequently the use of at least one sulphonic acid or a hydrate thereof, in the free state or at least partially neutralized, in or for the preparation of a cosmetic or dermatological composition for promoting desquamation of the skin and/or for stimulating epidermal renewal and/or epidermal repair. This at least one sulphonic acid has the formula (I):

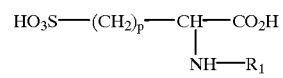

wherein p is 1 or 2 and $R_1$ represents a hydrogen atom or an acyl residue having the structure $—COR_2$ wherein $R_2$ is a linear or branched $C_1–C_{19}$ alkyl or alkenyl group. which is unsubstituted or substituted by at least one hydroxyl functional group.

Desquamation of the skin is associated with a clinical improvement in the quality of the skin which becomes more radiant, less wrinkled and generally younger in appearance. Moreover, the above sulphonic acids or hydrates thereof can be used to treat imperfections of the skin, such as blemishes, cutaneous dyschromias, dermatites, actinic lentigines, scars and cicatricial pigmentations.

A further subject of the invention is consequently the use of at least one sulphonic acid or hydrate thereof, in the free state or at least partially neutralized, for the preparation of a cosmetic or dermatological composition useful as an anti-aging agent, in particular for combatting at least one condition selected from wrinkles, fine lines, actinic blemishes, cutaneous dyschromias, dermatites, and scars.

The Inventor has, in particular, observed, without a full explanation for this being available, that these compounds can have an anti-aging action which is at least as effective as the compounds of the prior art which are all carboxylic acids. It has also been observed that, compared to compounds of the prior art, this action can also be milder, insofar as little or no irritation is experienced and little or no redness is observed, when a cosmetic or dermatological composition containing them is applied to the skin.

In particular, the acids of the invention include cysteic and homocysteic acids. These two acids have the advantage of being commercially available. The other acids of the invention can be prepared according to known methods. For example, the products of formula (I), wherein $R_1$ represents H, can be reacted with an activated form of an acid having the formula $R_2—COOH$, with $R_2$ being defined as indicated above, which can be an anhydrous product, a mixed anhydride (obtained from a chloroformate) or an acid chloride ($ClCOR_2$), the pH being maintained at a value within the range from 7 to 9 (i.e., a Schotten-Baumann reaction). At the end of the reaction, the product obtained is precipitated at an acidic pH (pH=1) or extracted according to conventional techniques.

All or part of the acids of the invention can be neutralized to form a salt, in particular by sodium hydroxide, potassium hydroxide, ammonia, monoethanolamine, triethanolamine and isopropanolamine.

In the compositions according to the invention, the sulphonic acid or the mixture of sulphonic acids, including the hydrates thereof, are used in an amount effective to achieve the purpose desired, and are preferably used in an amount ranging from 0.2 to 20% by weight with respect to the total weight of the composition, more preferably in an amount ranging from 0.5 to 10% and, most preferably, in an amount ranging from 0.5 to 5% by weight with respect to the total weight of the composition.

The acids of the invention can be combined with other active agents known for their desquamating properties, such as hydroxy acids, α- or β-keto acids or retinoids. Such a combination makes it possible to decrease the active concentration of these latter active agents, due to additive effects. It is thus possible to obtain a less irritating and less toxic composition as well as a composition which is more effective than those of the prior art in which only these active agents are used.

The hydroxy acids which can be used in accordance with the present invention include, for example, α-hydroxy acids and β-hydroxy acids, which can be linear, branched or cyclic, and saturated or unsaturated. The hydrogen atoms of the carbon chain can, in addition, be substituted by halogens or alkyl, acyl, acyloxy, alkoxycarbonyl or alkoxy radicals having from 2 to 18 carbon atoms.

These hydroxy acids are, in particular, glycolic, lactic, malic, tartaric and citric acids, and generally fruit acids, or 2-hydroxyalkanoic, mandelic and salicylic acids and their alkyl or acyl derivatives, such as 5-(n-octanoyl)salicylic acid, 5-(n-dodecanoyl)salicylic acid, 5-(n-decanoyl)salicylic acid, 5-(n-octyl)salicylic acid, 5- or 4-(n-heptyloxy)salicylic acid or 2-hydroxy-3-methylbenzoic acid, or alternatively their alkoxy derivatives, such as 2-hydroxy-3-methoxybenzoic acid.

The retinoids which can be used in accordance with the present invention include, in particular, retinoic acid (all trans or 13-cis) and its derivatives, retinol (vitamin A) and its esters, such as retinol palmitate, retinol acetate and retinol propionate, and their salts, or alternatively retinal.

By way of example, the hydroxy acids, the keto acids and the retinoids can be used in the compositions according to the invention in an amount preferably representing from 0.1 to 5% by weight of the total weight of the composition and, more preferably, from 0.5 to 3%.

For the purpose of effectively combatting photoaging, it is additionally possible to add, to the composition of the invention, one or a number of additional hydrophilic or lipophilic sunscreening agents which are active in the UVA and/or the UVB range.

An in vitro test of the effectiveness of the desquamation achieved in accordance with the present invention has been carried out on keratinocytes by using 5-(n-octanoyl)salicylic acid (compound 1), cysteic acid (compound 2, in accordance with the invention), the bis[1-(ethoxycarbonyl)ethyl] ester of nonanedioic acid (compound 3), 2-acetoxy-5-octanoylbenzoic acid (compound 4) and 5-oxothiomorpholine-3-carboxylic acid (compound 5).

The principle of the test, which is art-recognized and thus accepted by those skilled in the art, is based on the fact that desquamation induces the release of corneocytes. The greater the desquamating power of the tested product, the greater the number of corneocytes released.

The protocol of the test was as follows: keratinocytes were obtained from skin biopsies by separation from the epidermis, were dissociated by enzymatic action with trypsin and cultured at a concentration of $2 \times 10^{-5}$ cells/ml. Growth and differentiation of the keratinocytes were obtained by culturing for 10 to 20 days in a specific medium.

After removal of the culture medium, the test product was then added and the activity of the product evaluated. To do this, two samples were taken at $T_0$ and $T_{60}$, that is to say before the addition of the product and 60 minutes after this addition, and the samples thus taken were analyzed in a flow cytometer in order to count the population of corneocytes. The corneocyte and keratinocyte populations are differentiated in the flow cytometer by treatment with acridine orange (which is specific for the DNA of the cells) which binds to the nuclei of the cells and thus reveals the presence of the keratinocytes exclusively.

The cell detachment index is determined by the differences between $T_{60}$ and $T_0$.

The same measurement, i.e., the cell detachment index, was determined for a control which contained no test product because the experiment inevitably results in the release of corneocytes, even in the absence of active agent.

The results are collated in the table below:

| Control | Compound 1 | Compound 2 | Compound 3 | Compound 4 | Compound 5 |
| --- | --- | --- | --- | --- | --- |
| 0% | 106% | 206% | 59% | inactive | inactive |

These results clearly show that Compound 2, cysteic acid, at the same concentration as Compound 1, 5-(n-octanoyl) salicylic acid, which is known to be a powerful desquamating active agent, is much more active than the latter and that the other compounds have significantly lower activities than cysteic acid.

A further subject of the invention is a process for the cosmetic or dermatological treatment of the skin for the purpose of desquamation of the skin, which comprises applying to the skin a composition containing at least one sulphonic acid of formula (I) or a hydrate thereof, in the free state or partially neutralized, preferably in a cosmetically and/or dermatologically acceptable medium.

Another subject of the invention is a process for the cosmetic or dermatological treatment of aging of the skin, which comprises applying to the skin a composition containing at least one sulphonic acid or a hydrate thereof as defined above, preferably in a cosmetically and/or dermatologically acceptable medium.

A still further subject of the invention is a process for the cosmetic or dermatological treatment of various conditions of the skin including, but not limited to, wrinkles, fine lines, actinic blemishes, cutaneous dyschromias, scars and dermatites, which comprises applying to the skin a composition containing at least one sulphonic acid or a hydrate thereof as defined above, preferably in a cosmetically and/or dermatologically acceptable medium.

The compositions of the invention preferably contain a cosmetically or dermatologically acceptable medium, that is to say a medium compatible with the skin, the nails, the mucous membranes, the tissues and the hair. The composition containing sulphonic acid can be applied topically to the face, the neck, the hair, the mucous membranes and the nails or any other cutaneous region of the body.

The compositions according to the invention can be provided in any form appropriate for topical application, in particular in the form of aqueous, aqueous/alcoholic or oily solutions; dispersions of the lotion or serum type; aqueous, anhydrous or oily gels; emulsions with a liquid or semi-liquid consistency of the milk type, obtained by dispersion of a fatty phase in an aqueous phase (O/W) or vice versa (W/O); suspensions or emulsions with a soft, semi-solid or solid consistency of the cream or gel type; microemulsions, microcapsules, microparticles or vesicular dispersions of the ionic and/or nonionic type. These compositions can be prepared according to conventional methods.

The compositions of the invention can also be used for the hair in the form of aqueous, alcoholic or aqueous/alcoholic solutions or in the form of creams, gels, emulsions or foams or in the form of aerosol compositions also containing a pressurized propellant agent.

The amounts of the various other constituents of the compositions according to the invention are those conventionally used in the fields under consideration.

These compositions preferably constitute protective, treatment or care creams for the face, for the hands or for the body, protective or care body milks, lotions, gels or foams for caring for the skin and mucous membranes or for cleansing the skin.

The compositions can also comprise solid preparations comprising cleansing bars or soaps.

When the composition of the invention is an emulsion, the proportion of the fatty phase preferably ranges from 5% to 80% by weight, and more preferably ranges from 5% to 50% by weight, with respect to the total weight of the composition. The oils, the emulsifiers and the coemulsifiers used in the composition in the emulsion form are chosen from those conventionally used in the cosmetics or dermatological field.

The emulsifier and the coemulsifier are preferably present, in the composition, in a proportion ranging from 0.3% to 30% by weight, and more preferably ranging from 0.5 to 20% by weight, with respect to the total weight of the composition. The emulsion can, in addition, contain lipid vesicles.

When the composition is an oily solution or an oily gel, the amount of oil preferably ranges up to more than 90% by weight of the total weight of the composition.

In a known way, the composition of the invention can also contain adjuvants which are conventional in the cosmetics and dermatological fields, such as hydrophilic or lipophilic gelling agents, hydrophilic or lipophilic active agents, preservatives, antioxidants, solvents, fragrances, fillers and colouring materials.

The amounts of these various adjuvants are those conventionally used in the fields under consideration, for example from 0.01% to 20% of the total weight of the composition. These adjuvants, depending on their nature, can be introduced into the fatty phase, into the aqueous phase and/or into the lipid spherules.

Mention may be made, as oils which are preferably used in accordance with the invention, of mineral oils (liquid petrolatum), vegetable oils (karite oil, sweet almond oil), animal oils, synthetic oils, silicone oils (cyclomethicone) and fluorinated oils (perfluoropolyethers). It is also possible to use, as fatty substances, fatty alcohols, fatty acids (stearic acid) and waxes (paraffin wax, carnauba wax, beeswax).

Mention may be made, as emulsifiers which can preferably be used in accordance with the invention, of Polysorbate 60 and sorbitan stearate sold respectively under the trade names Tween 60 and Span 60 by the Company ICI. Coemulsifiers, such as PPG-3 myristyl ether sold under the trade name Emcol 249-3K by the company Witco, can be added thereto.

Mention may be made, as solvents which can preferably be used in the invention, of lower alcohols, in particular ethanol and isopropanol, or propylene glycol.

Mention may be made, as hydrophilic gelling agents, of carboxyvinyl polymers (carbomer), acrylic copolymers, such as acrylate/alkyl acrylate copolymers, polyacrylamides, polysaccharides, such as hydroxypropylcellulose, natural gums (xanthan gum) and clays; mention may be made, as lipophilic gelling agents, of modified clays, such as bentones, metal salts of fatty acids, such as aluminium stearates, hydrophobic silica, polyethylenes and ethylcellulose.

It is possible to use, as hydrophilic active agents, proteins or protein hydrolysates, amino acids, polyols, urea, allantoin, sugars and sugar derivatives, water-soluble vitamins, starch, or bacterial or plant extracts, in particular, Aloe vera.

It is possible to use, as lipophilic active agents, tocopherol (vitamin E) and its derivatives, essential fatty acids, ceramides or essential oils.

It is possible, inter alia, to combine the sulphonic acids with active agents intended in particular for the prevention and/or the treatment of cutaneous ailments. Mention may be made, among these active agents, by way of example, of:

agents which modify cutaneous differentiation and/or proliferation and/or pigmentation, such as vitamin D and its derivatives, oestrogens, such as oestradiol, kojic acid or hydroquinone;

agents for combatting free radicals, such as a-tocopherol or its esters, superoxide dismutases, certain metal chelating agents or ascorbic acid and its esters.

The cosmetic or dermatological treatment processes of the invention can be implemented in particular by applying the hygienic, cosmetic or dermatological compositions as defined above according to the usual technique for the use of these compositions, for example: application of creams, gels, serums, ointments, lotions or milks to the skin, the scalp, the nails and/or the mucous membranes.

The following examples illustrate the invention. In these examples, the proportions shown are percentages by weight.

EXAMPLE 1

Preparation of an Oil-in-Water Emulsion

| Phase A: | |
| --- | --- |
| Cysteic acid | 2.5 |
| Sweet almond oil | 14.5 |
| Karite oil | 7.0 |
| PPG-3 myristyl ether (Emcol 249-3K) | 5.0 |
| Preservative (propylparaben) | 0.1 |
| Polysorbate 60 (Tween 60) | 2.5 |
| Sorbitan stearate (Span 60) | 2.5 |
| Phase B: | |
| Cyclomethicone | 4.0 |
| Xanthan gum | 0.2 |
| Carboxyvinyl polymer | 0.5 |
| Phase C: | |
| Triethanolamine (neutralizing agent) | 0.5 |
| Water | 2.0 |

-continued

| Phase D: | |
|---|---|
| Preservative (methylparaben) | 0.2 |
| Glycerol | 5.0 |
| Water | q.s. for 100 |

Procedure:

The constituents of phase A were melted at 85° C., phase A was then cooled to 70° C. and phases B, and then C and D, were introduced therein with stirring. Cooling was carried out to room temperature. A day cream was obtained which caused desquamation of the skin and thus conferred a smoother and younger appearance on the skin than existed before the treatment.

EXAMPLE 2
Preparation of a Gel

| Homocysteic acid | 5.0 |
|---|---|
| Hydroxypropylcellulose (Klucel H from the company Hercules) | 1.0 |
| Antioxidant | 0.05 |
| Isopropanol | 40.0 |
| Preservative | 0.3 |
| Water | q.s. for 100 |

A gel was obtained which, on regular application, toned down blemishes of the skin by desquamation.

EXAMPLE 3
Preparation of a Solution for Dermatological Application

| Cysteic acid | 5.00 |
|---|---|
| Antioxidant | 0.05 |
| Ethyl alcohol | 10.00 |
| Preservative | 0.30 |
| Water | q.s. for 100 |

The application under dermatological control of this solution brought-about deep desquamation of the corneal layer and, thus, instigated an epidermal repair process which resulted in, as final therapeutic effect, an erasing of blemishes and dyschromias, a toning down of wrinkles and fine lines and an improvement in the clinical condition of the skin, the appearance of which became that of a younger skin. This application was carried out one to three times weekly for 4 to 6 weeks.

What is claimed is:

1. A method for stimulating epidermal renewal, which comprises the step of contacting the skin with a cosmetic or dermatological composition, said cosmetic or dermatological composition containing an amount effective to stimulate epidermal renewal and/or epidermal repair of at least one sulphonic acid or a hydrate thereof, said at least one sulphonic acid being in the free state or being at least partially neutralized and having the formula (I):

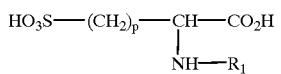
(I)

wherein p is 1 or 2 and $R_1$ represents a hydrogen atom or an acyl residue having the structure —$COR_2$, wherein $R_2$ is a linear or branched $C_1$–$C_{19}$ alkyl or alkenyl group which is unsubstituted or substituted by at least one hydroxyl functional group, wherein said composition additionally comprises at least one active agent selected from α-hydroxy acids, β-hydroxy acids, α-keto acids, β-keto acids and retinoids.

2. A method for stimulating epidermal renewal according to claim 1, wherein said at least one sulphonic acid is selected from cysteic acid, homocysteic acid and hydrates thereof.

3. A method for stimulating epidermal renewal according to claim 1, wherein said effective amount of said at least one sulphonic acid or hydrate thereof is an amount ranging from 0.2 to 20% by weight with respect to the total weight of the composition.

4. A method for stimulating epidermal renewal according to claim 3, wherein said effective amount of said at least one sulphonic acid or hydrate thereof is an amount ranging from 0.5 to 5% by weight with respect to the total weight of the composition.

5. A method for stimulating epidermal renewal according to claim 1, wherein said composition additionally comprises at least one active agent selected from glycolic, lactic, malic, tartaric, citric, 2-hydroxyalkanoic, mandelic, salicylic and 5-(n-octanoyl)salicylic acids.

6. A method for stimulating epidermal renewal according to claim 1, wherein said active agent is present in an amount ranging from 0.1 to 5% by weight with respect to the total weight of the composition.

7. A method for stimulating epidermal renewal according to claim 5, wherein said active agent is present in an amount ranging from 0.1 to 5% by weight with respect to the total weight of the composition.

8. A method for stimulating epidermal renewal according to claim 1, wherein said composition additionally comprises at least one adjuvant selected from proteins, protein hydrolysates, amino acids, polyols, urea, sugars, sugar derivatives, vitamins, starch, plant extracts, essential fatty acids, ceramides and essential oils.

9. A method for stimulating epidermal renewal according to claim 1, wherein said composition is an aqueous solution, an oily solution, an aqueous/alcoholic solution, a water-in-oil emulsion, an oil-in-water emulsion, a microemulsion, an aqueous gel, an anhydrous gel, a serum, a dispersion of vesicles, a dispersion of microcapsules or a dispersion of microparticles.

10. A method for combatting cutaneous aging, which comprises the step of contacting the skin with a cosmetic or dermatological composition, said cosmetic or dermatological composition containing an amount effective to combat cutaneous aging of at least one sulphonic acid or a hydrate thereof, said at least one sulphonic acid being in the free state or being at least partially neutralized and having the formula (I):

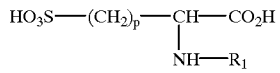

wherein p is 1 or 2 and $R_1$ represents a hydrogen atom or an acyl residue having the structure —$COR_2$, wherein $R_2$ is a linear or branched $C_1$–$C_{19}$ alkyl or alkenyl group which is unsubstituted or substituted by at least one hydroxyl functional group,
wherein said composition additionally comprises at least one active agent selected from α-hydroxy acids, β-hydroxy acids, α-keto acids, β-keto acids and retinoids.

11. A method for combatting cutaneous aging according to claim 10, wherein said at least one sulphonic acid is selected from cysteic acid, homocysteic acid and hydrates thereof.

12. A method for combatting cutaneous aging according to claim 10, wherein said effective amount of at least one sulphonic acid or hydrate thereof is an amount ranging from 0.2 to 20% by weight with respect to the total weight of the composition.

13. A method for combatting cutaneous aging according to claim 12, wherein said effective amount of said at least one sulphonic acid or hydrate thereof is an amount ranging from 0.5 to 5% by weight with respect to the total weight of the composition.

14. A method for combatting cutaneous aging according to claim 10, wherein said composition additionally comprises at least one active agent selected from glycolic, lactic, malic, tartaric, citric, 2-hydroxyalkanoic, mandelic, salicylic and 5-(n-octanoyl)salicylic acids.

15. A method for combatting cutaneous aging according to claim 10, wherein said active agent is present in an amount ranging from 0.1 to 5% by weight with respect to the total weight of the composition.

16. A method for combatting cutaneous aging according to claim 14, wherein said active agent is present in an amount ranging from 0.1 to 5% by weight with respect to the total weight of the composition.

17. A method for combatting cutaneous aging according to claim 10, wherein said composition additionally comprises at least one adjuvant selected from proteins, protein hydrolysates, amino acids, polyols, urea, sugars, sugar derivatives, vitamins, starch, plant extracts, essential fatty acids, ceramides and essential oils.

18. A method for combatting cutaneous aging according to claim 10, wherein said composition is an aqueous solution, an oily solution, an aqueous/alcoholic solution, a water-in-oil emulsion, an oil-in-water emulsion, a microemulsion, an aqueous gel, an anhydrous gel, a serum, a dispersion of vesicles, a dispersion of microcapsules or a dispersion of microparticles.

19. A method for combatting at least one skin condition selected from wrinkles, fine lines, actinic blemishes, cutaneous dyschromias, scars, and dermatites, which comprises the step of contacting the skin with a cosmetic or dermatological composition, said cosmetic or dermatological composition containing an amount effective to combat at least one of said skin conditions of at least one sulphonic acid or a hydrate thereof, said at least one sulphonic acid being in the free state or being at least partially neutralized and having the formula (I):

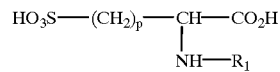

wherein p is 1 or 2 and $R_1$ represents a hydrogen atom or an acyl residue having the structure —$COR_2$, wherein $R_2$ is a linear or branched $C_1$–$C_{19}$ alkyl or alkenyl group which is unsubstituted or substituted by at least one hydroxyl functional group, wherein said composition additionally comprises at least one active agent selected from α-hydroxy acids, β-hydroxy acids, α-keto acids, β-keto acids and retinoids.

20. A method for combatting a least one skin condition according to claim 19, wherein said at least one sulphonic acid is selected from cysteic acid, homocysteic acid and hydrates thereof.

21. A method for combatting at least one skin condition according to claim 19, wherein said effective amount of said at least one sulphonic acid or hydrate thereof is an amount ranging from 0.2 to 20% by weight with respect to the total weight of the composition.

22. A method for combatting at least one skin condition according to claim 21, wherein said effective amount of said at least one sulphonic acid or hydrate thereof is an amount ranging from 0.5 to 5% by weight with respect to the total weight of the composition.

23. A method for combatting at least one skin condition according to claim 19, wherein said composition additionally comprises at least one active agent selected from α-hydroxy acids, β-hydroxy acids, α-keto acids, β-keto acids and retinoids.

24. A method for combatting at least one skin condition according to 19, wherein said composition additionally comprises at least one active agent selected from glycolic, lactic, malic, tartaric, citric, 2-hydroxyalkanoic, mandelic, salicylic and 5-(n-octanoyl)salicylic acids.

25. A method for combatting at least one skin condition according to claim 23, wherein said active agent is present in an amount ranging from 0.1 to 5% by weight with respect to the total weight of the composition.

26. A method for combatting at least one skin condition according to claim 24, wherein said active agent is present in an amount ranging from 0.1 to 5% by weight with respect to the total weight of the composition.

27. A method for combatting at least one skin condition according to claim 19, wherein said composition additionally comprises at least one adjuvant selected from proteins, protein hydrolysates, amino acids, polyols, urea, sugars, sugar derivatives, vitamins, starch, plant extracts, essential fatty acids, ceramides and or essential oils.

28. A method for combatting at least one skin condition according to claim 19, wherein said composition is an aqueous solution, an oily solution, an aqueous/alcoholic solution, a water-in-oil emulsion, an oil-in-water emulsion, a microemulsion, an aqueous gel, an anhydrous gel, a serum, a dispersion of vesicles, a dispersion of microcapsules or a dispersion of microparticles.

\* \* \* \* \*